United States Patent [19]
Saito et al.

[11] Patent Number: 6,021,339
[45] Date of Patent: Feb. 1, 2000

[54] URINE TESTING APPARATUS CAPABLE OF SIMPLY AND ACCURATELY MEASURING A PARTIAL URINE TO INDICATE URINARY GLUCOSE VALUE OF TOTAL URINE

[75] Inventors: Atsushi Saito; Soichi Saito; Masako Miyazaki, all of Tokyo, Japan

[73] Assignee: NEC Corporation, Tokyo, Japan

[21] Appl. No.: 09/161,648

[22] Filed: Sep. 28, 1998

[30] Foreign Application Priority Data

Sep. 26, 1997 [JP] Japan .................................. 9-262387

[51] Int. Cl.[7] ...................................................... A61N 5/00
[52] U.S. Cl. ............................................ 600/345; 600/365
[58] Field of Search .................................. 600/345, 300, 600/365; 128/897–898, 899

[56] References Cited

U.S. PATENT DOCUMENTS

| | | | |
|---|---|---|---|
| 4,381,895 | 5/1983 | Hughes et al. | 356/134 |
| 5,556,760 | 9/1996 | Nakamura et al. | 435/12 |
| 5,602,038 | 2/1997 | Kell | 436/98 |
| 5,776,783 | 7/1998 | Kell | 436/111 |
| 5,837,454 | 11/1998 | Cozette et al. | 435/6 |

*Primary Examiner*—Cary O'Connor
*Assistant Examiner*—Michael Astorino
*Attorney, Agent, or Firm*—Sughrue, Mion, Zinn, Macpeak & Seas, PLLC

[57] ABSTRACT

A urine multisensor has a sensor element to detect components to be measured, that has a urea component detecting unit and at least one of a detection unit of sodium ions and a detection unit of chloride ions to detect these components contained in urine, so as to know urine specific gravity on the basis of the concentration of each component yielded from the detection signal. Besides, a detection unit of glucose component is added in necessity to add a structure to correct a urinary glucose value (glucose level) with the urine specific gravity finally resulting in that the urinary glucose value of total urine excreted for 24 hours can be simply and accurately known from the partial urine.

15 Claims, 8 Drawing Sheets

URINE TESTING APPARATUS CAPABLE OF SIMPLY AND ACCURATELY MEASURING A PARTIAL URINE TO INDICATE URINARY GLUCOSE VALUE OF TOTAL URINE

BACKGROUND OF THE INVENTION

The present invention relates to a urine testing apparatus, and particularly to a urine testing apparatus capable of obtaining accurate urine specific gravity and urine glucose level (urinary glucose value).

In the point of test and therapy of diabetes, it is important to know urine glucose level (urinary glucose value). The urinary glucose value is, as a rule, evaluated by measuring glucose amount contained in total urine excreted for 24 hours (total excreted urine). Practically, the urinary glucose value is measured after urine is accumulated for one day (accumulation of urine) in a container. However, operation of these steps is complicated allowing to apply to hospitalized patients only. In contrast to the total excreted urine, once excreted urine is named partial urine (urine excreted in each individual occasion). At present, in outpatients, group examination, and home therapy, the measurement of the urinary glucose value of the total excreted urine has been replaced by that of the partial urine, using urine test paper or a urinary glucose meter. However, the urinary glucose value changes according to urine amount to result in occasional inconsistency between urinary glucose values of the partial urine and total excreted urine. This defect causes inaccurate diagnosis.

Therefore, a method has been proposed to measure and correct the urinary glucose value of the partial urine. For example, in a journal (Igaku Kensa 43: 1839–1845. 1994), it has been reported that measurement is carried out for urine specific gravity of the partial urine and urinary glucose value of the partial urine is corrected with the urine specific gravity on the basis of the following formula (1) to estimate the urinary glucose value of total excreted urine.

$$\text{Urinary glucose value (specific gravity corrected)} = \text{urinary glucose value of partial urine} \times (1.015 - 1.000) / (\text{urine specific gravity of partial urine} - 1.000) \quad (1)$$

wherein 1.015 means the standard value of the urine specific gravity in urine accumulation for 24 hours.

In Unexamined Japanese Patent Publication No.9262/1991, a urine testing apparatus is disclosed to indicate the critical degree of diabetes through the fuzzy processing of the result of the measurement of urinary glucose value, urine pH, and urine specific gravity of the partial urine. In the urine testing apparatus disclosed therein, measuring methods of the urinary glucose value and the urine pH are an optical reading method for the coloring degree of test paper of coloring reaction and a method of electric detection using an enzyme electrode. However, any measuring method of the urine specific gravity has never been described. Besides, a relationship between the urinary glucose value and the urine specific gravity has not described, but a fuzzy processing has been only presented in the publication.

In the interim, weight method, areometry, falling method, and refractometry is commonly known for measurement of urine specific gravity. Though these methods are accurate, requires expensive measuring instruments and are time-consuming for operation. Thus, an indirect method based on chemical properties has been invented. This method named test paper method for specific gravity is done by measuring a cation concentration in urine to read specific gravity from the correlation of the cation concentration and specific gravity. For example, macromolecular electrolyte (methoxyethylene—maleic acid anhydride copolymer), buffer solution, and pH indicator (bromothymol blue: yellow color changes to blue at pH 6.2–7.8) are applied to a base material. Cations contained in urine is substituted by hydrogen ions of the macromolecular electrolyte to release hydrogen ions resulting in pH change that is detected with pH indicator. However, it is currently difficult to yield the urine specific gravity from cation concentration due to the changed eating habits of Japanese people. Therefore, a proposal of measuring method using test paper was made for knowing the urine specific gravity from urine concentration (the publication of patent applications 1993-180846). For example, coloring test tool is constituted by attaching a base material such as filter paper, to which urease, pH indicator, and buffer solution have been applied, to a supporter such as polystylene. Urea contained in urine is decomposed by urease on the coloring test tool. PH changed by ammonia generated by the decomposition is detected with the pH indicator to measure urine concentration.

On the contrary, urine specific gravity is changed according to two components of sodium chloride (10–15 g/day) and urea (15–30 g/day) as principal solute components (Rinsyou Byouri. November extra issue: 98–108. 1995). Therefore, when cations or urea concentration is individually measured to know urine specific gravity on the basis of correlation, the gravity yielded probably has an error.

Prior art related to the measurement of urinary glucose value has the following defects.

First, the prior art does not allow to make simple and accurate measurement of urine specific gravity. The reason is that the estimation of urine specific gravity by measuring cations or urea concentration individually using test paper has the error, because urine specific gravity is primarily determined by sodium chloride concentration and urea concentration both contained in urine.

Second, the prior art does not allow to estimate simply urinary glucose value contained in total urine excreted for 24 hours on the basis of the urinary glucose value of a partial urine. The reason is that the urinary glucose value of a partial urine differs from the urinary glucose value contained in total urine excreted for 24 hours,because the former urinary glucose value is affected by urine volume.

SUMMARY OF THE INVENTION

It is therefore an object of the present invention to provide a urine testing apparatus capable of indication of the urinary glucose value of total urine excreted for 24 hours by correcting the urinary glucose value of the partial urine with the urine specific gravity on the basis of the simple and accurate measurement of the urine specific gravity and urinary glucose value of the partial urine.

Other objects of the present invention will become clear as the description proceeds.

According to an aspect of the present invention, there is provided a urine testing apparatus comprising: a sensor element, to detect components to be measured, having a urea detecting unit and at least one of a detection unit of sodium ions and a detection unit of chloride ions to detect urea and at least one of sodium ions and chloride ions that are components to be measured contained in urine; a signal processing unit for converting a signal generated by detecting each component to be measured in the sensor element to detect components to be measured to a concentration of each component to be measured and for calculating a specific gravity of the urine on the basis of these concentrations; and a display unit for displaying the urine specific gravity calculated in the signal processing unit and the concentration of at least one of the components to be measured.

In the urine testing apparatus, a voltage detecting circuit may detect a voltage signal generated by detecting the components to be measured using the sensor element to detect components to be measured and the signal processing unit may convert a detection signal of each component to be measured outputted from the voltage detecting circuit to the concentration of each component to be measured and calculates the urine specific gravity from the concentrations.

The urine testing apparatus may calculate the urine specific gravity on the basis of any one of a concentration of sodium ions or a concentration of chloride ions and a concentration of urea.

The urine detecting unit may comprise a measurement electrode and a reference electrode, that are formed on an insulated base material, and a urea detecting film formed on the measurement electrode and containing urease.

The measurement electrode may be an ion-sensitive field-effect transistor.

The sensor element, to detect components to be measured, may have both the detection unit of sodium ions and the detection unit of chloride ions in addition to the urea detecting unit, the detection unit of sodium ions, the detection unit of chloride ions and the urea detecting unit having a measurement electrode and a reference electrode formed on an insulated base material and a film for detecting components to be measured, that contains a substance sensitive to sodium ions and a substance sensitive to chloride ions formed on the measurement electrode.

The measurement electrode may be an ion-sensitive field-effect transistor.

According to another aspect of the present invention, there is provided a urine testing apparatus comprising: a sensor element, to detect components to be measured, having a glucose detecting unit, a urea detecting unit, and at least one of a detection unit of sodium ions and a detection unit of chloride ions to detect glucose, urea and at least one of sodium ions and chloride ions that are components to be measured contained in urine; a signal processing unit for converting a signal generated by detecting each component to be measured in the sensor element to detect components to be measured to a concentration of each component to be measured and for calculating a specific gravity of the urine on the basis of a concentration of urea and at least one of a concentration of sodium ions and a concentration of chloride ions to correct the concentration of glucose with the urine specific gravity obtained; and a display unit for displaying the glucose concentration corrected in the signal processing unit, and at least one of the urine specific gravity, the urea concentration, a concentration of sodium ions and a concentration of chloride ions.

In the urine testing apparatus, a current detecting circuit may detect a current signal generated by detecting glucose with the sensor element to detect components to be measured, a voltage detecting circuit may detect a voltage signal generated by detecting urea and at least one of sodium ions and chloride ions, and the signal processing unit may convert the current and the voltage signals outputted from the current detecting circuit and the voltage detecting circuit into the concentration of each component to be measured, respectively, and calculates the urine specific gravity and a glucose concentration corrected by the urine specific gravity on the basis of the concentrations.

The sensor element to detect components to be measured may have a glucose detecting unit, a urine detecting unit, and any one of a detection unit of sodium ions and a detection unit of chloride ions to calculate the urine specific gravity on the basis of any one of a concentration of sodium ions and a concentration of chloride ions, and the urea concentration.

The glucose detecting unit may have a structure comprising a measurement electrode and a reference electrode, that are formed on an insulated base material, and a detecting film, that is formed on the electrode, for components to be measured including glucose oxidase and the measurement electrode may be a working electrode or a working electrode and a counter electrode.

The urine detecting unit may comprise a measurement electrode and a reference electrode, that are formed on an insulated base material, and a urea detecting film formed on the measurement electrode and containing urease.

The measurement electrode may be an ion-sensitive field-effect transistor.

The sensor element, to detect components to be measured, may have both the detection unit of sodium ions and the detection unit of chloride ions in addition to the urea detecting unit, the detection unit of sodium ions, the detection unit of chloride ions and the urea detecting unit having a measurement electrode and a reference electrode formed on an insulated base material and a film for detecting components to be measured, that contains a substance sensitive to sodium ions and a substance sensitive to chloride ions formed on the measurement electrode.

The measurement electrode may be an ion-sensitive field-effect transistor.

DETAILED DESCRIPTION OF THE PREFERRED EMBODIMENTS

Figure 1:
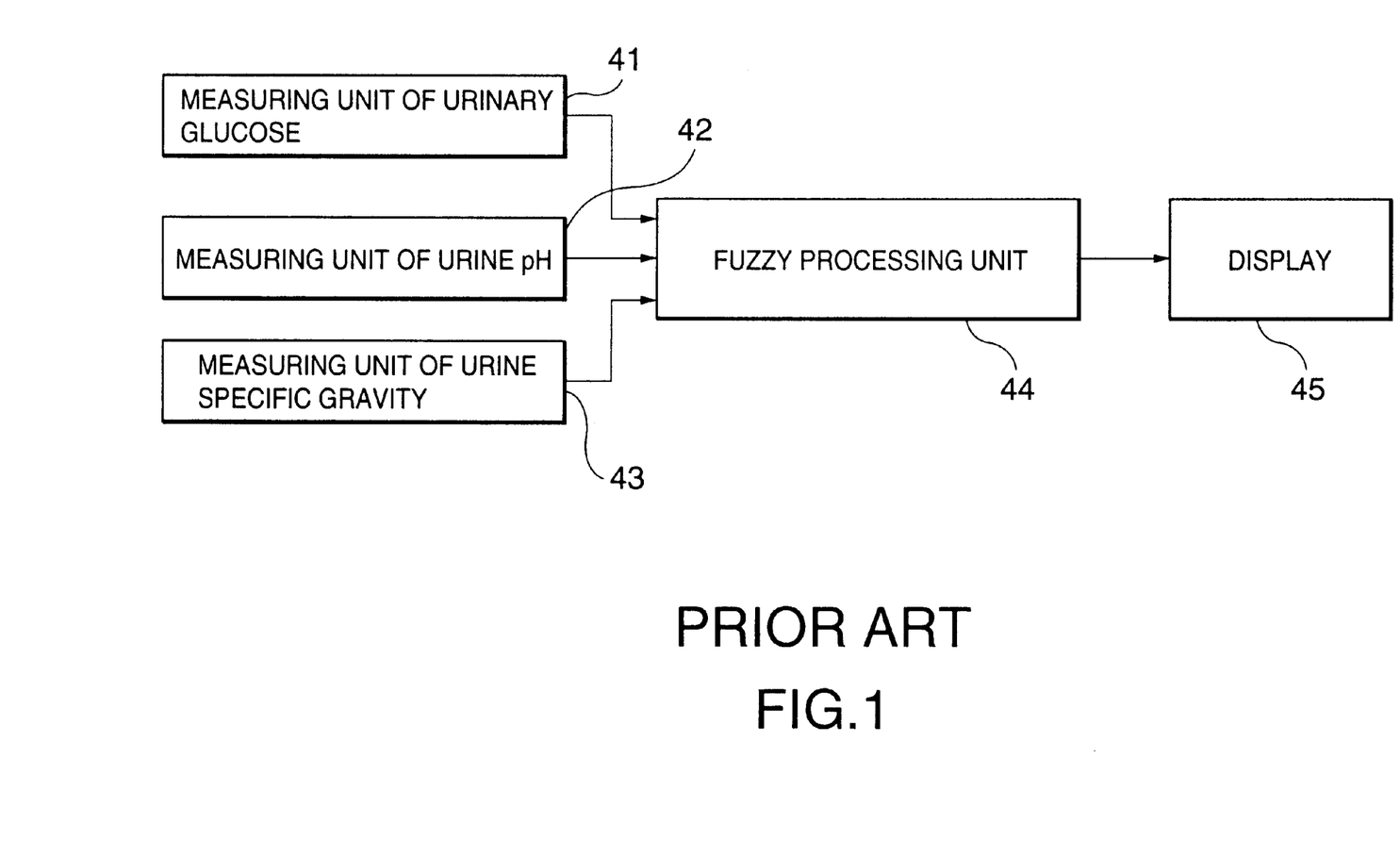
FIG. 1 is a block diagram for showing a structure of a conventional urine testing apparatus.

Referring to FIG. 1, description is, at first made about a conventional urine testing apparatus which is disclosed in the above-mentioned Unexamined Japanese Patent Publication No.9262/1991 in order to facilitate an understanding of the present invention.

FIG. 1 is a block diagram for showing a structure of the conventional urine testing apparatus. In the conventional urine testing apparatus illustrated in FIG. 1, urinary glucose value, urine pH, and urine specific gravity measured by the measuring unit of urinary glucose value 41, the measuring unit of urine ph 52, and the measuring unit of urine specific gravity 43 is inputted to the fuzzy processing unit 44 to yield the critical degree of diabetes through fuzzy inference. A display 45 indicates the urinary glucose value, the urine pH, the urine specific gravity, and the critical degree of diabetes.

As mentioned in the preamble of the instant specification, measuring methods of the urinary glucose value and the urine pH stated for this apparatus are an optical reading method for the coloring degree of test paper of coloring reaction and a method of electric detection using an enzyme electrode. However, any measuring method of the urine specific gravity has never been described. Besides, a relationship between the urinary glucose value and the urine specific gravity has not described, but a fuzzy processing has been only presented in the publication.

Referring now to FIGS. 2 through 5C, description will proceed to a urine multisensor as a urine testing apparatus according to a first embodiment of the present invention.

Figure 2:
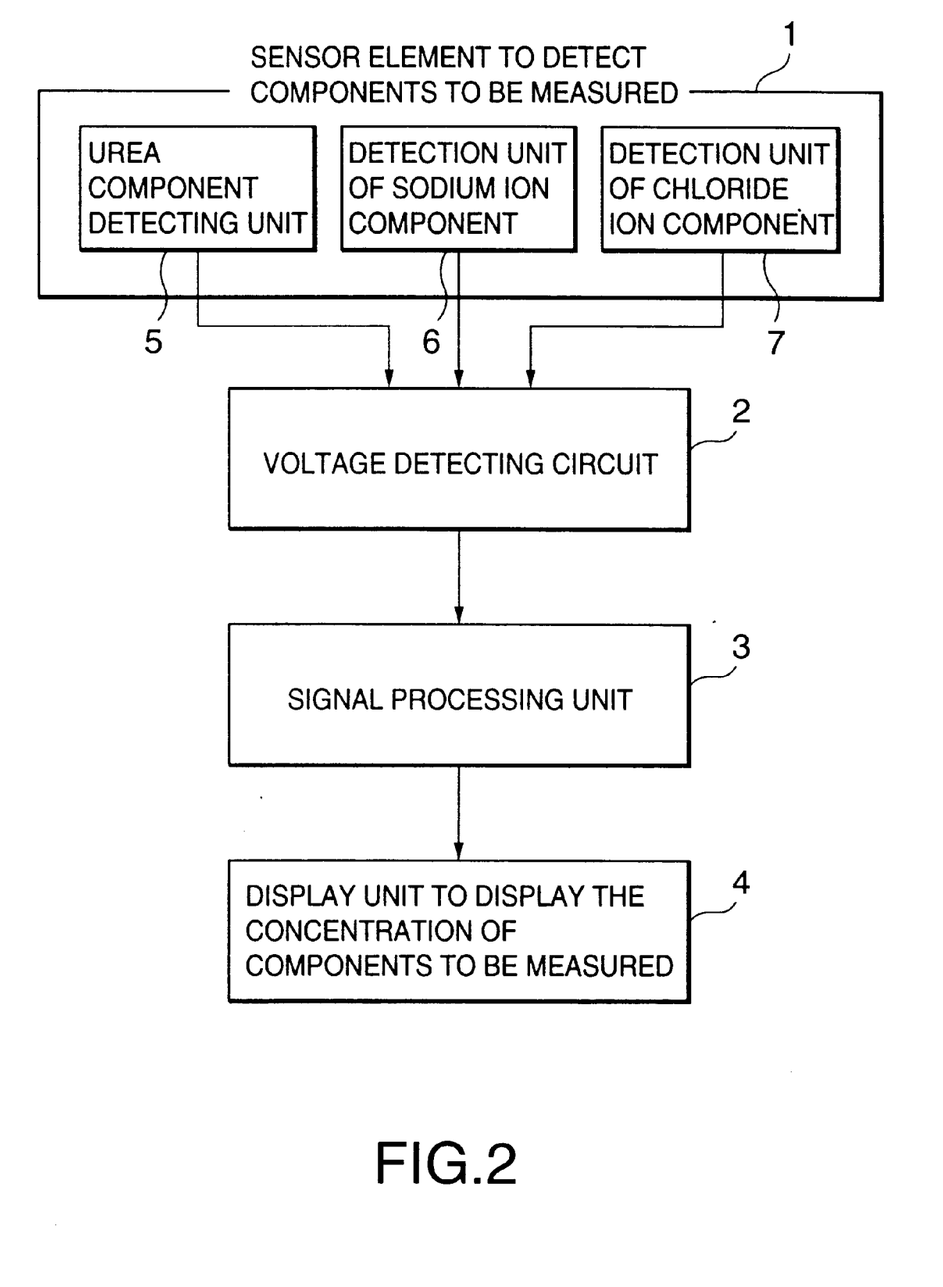
FIG. 2 is a block diagram for showing a structure of a urine testing apparatus for measurement of a urine specific gravity according to a first embodiment of the present invention.

FIG. 2 is a block diagram to explain a structure of the urine multisensor for the measurement of the urine specific gravity in the first embodiment of the present invention.

As illustrated in FIG. 2, the urine multisensor comprises a sensor element 1 to detect components to be measured, a voltage detecting circuit 2, signal processing unit 3, and a display unit 4. The sensor element 1 to detect components to be measured has urea detection unit 5, the detection unit of sodium ions 6, and the detection unit of chloride ions 7.

Figure 3:
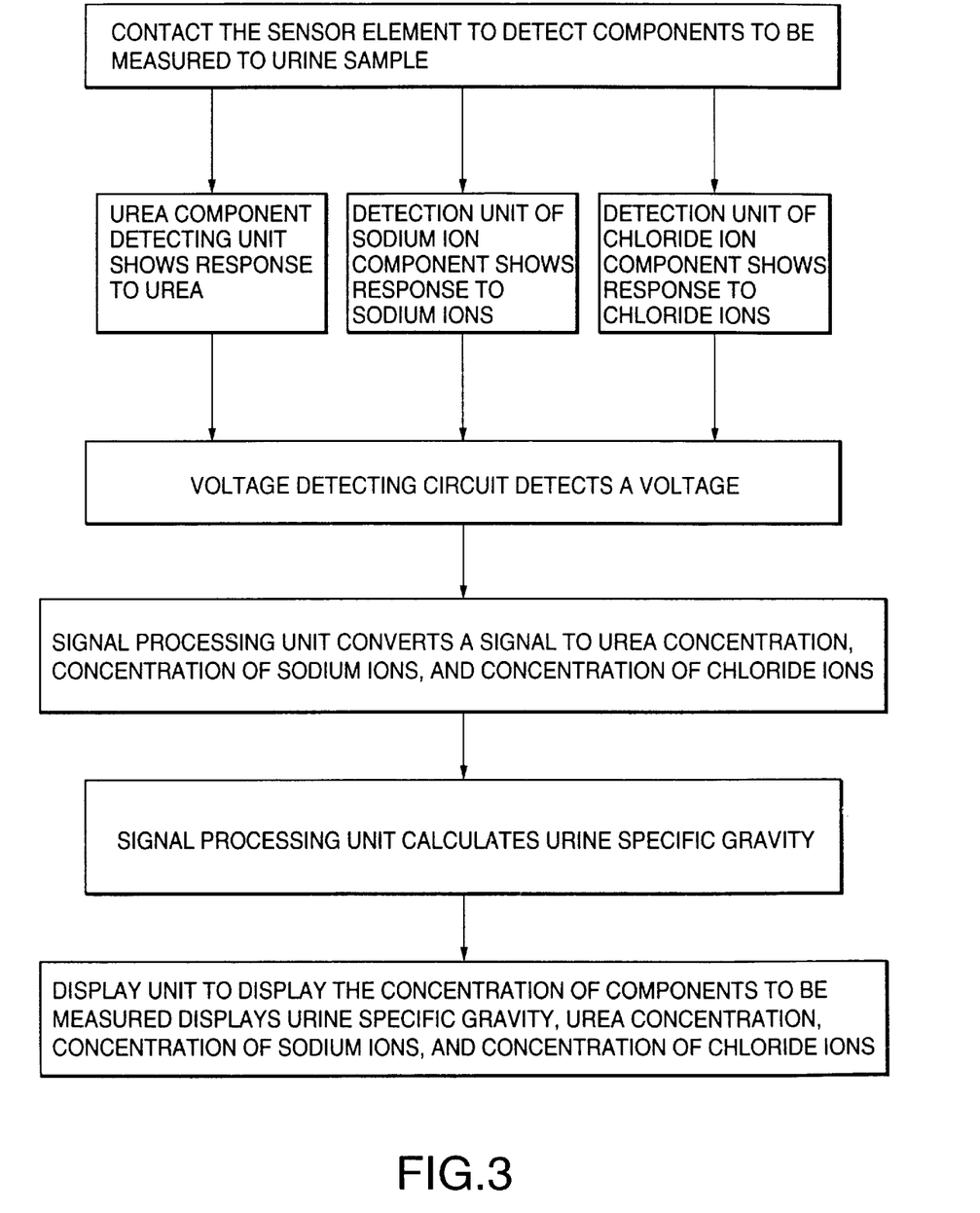
FIG. 3 is a flow chart for showing an operation of the urine testing apparatus illustrated in FIG. 2.

FIG. 3 is a flow chart to explain an operation of the urine multisensor of aforementioned structure. The measurement of urine specific gravity using the urine multisensor of the figure is described herewith. By contacting the sensor element of the urine multisensor to detect components to be measured to the sample of urine, the urea detection unit, the detection unit of sodium ions, and the detection unit of chloride ions show response to urea, sodium ions, and chloride ions contained in urine, respectively. As a result of the reaction, a voltage or the change of voltage occurred each in the urea detection unit, the detection unit of sodium ions, and the detection unit of chloride ions are detected through the voltage detecting circuit. In the signal processing unit, a signal outputted from the voltage detecting circuit is converted to the concentration of each component to detect. In addition, the urine specific gravity is calculated from the known concentrations on the basis of any one of the following formulae (2)–(4).

(a) Calculation from urea concentration a (mg/dl), sodium ions concentration b (mg/dl), and chloride ions concentration c (mg/dl):

$$\text{Urine specific gravity} = (a+b+c) \times f \times 10^{-5} \quad (2)$$

(b) Calculation from urea concentration a (mg/dl) and sodium ions concentration b (mg/dl):

$$\text{Urine specific gravity} = (a+b \times 58.5/23.0) \times f \times 10^{-5} \quad (3)$$

(c) Calculation from urea concentration a (mg/dl) and chloride ions concentration c (mg/dl):

$$\text{Urine specific gravity} = (a+c \times 58.5/35.5) \times f \times 10^{-5} \quad (4)$$

wherein f represents correction factor (use f=4.837).

The urine specific gravity, the urea concentration, sodium ions concentration, and chloride ions concentration measured and calculated are indicated on the display unit 4. For reference, it is optional that both these sodium ions concentration and chloride ions concentration are measured for calculation of the urine specific gravity to indicate these concentrations on the display unit and that any one of these concentrations is used for the calculation of the urine specific gravity to indicate these concentrations on the display unit.

If a performance necessary to the invention is achieved, the structure of each unit of the urine multisensor of the invention is not specially restricted. However, it is preferable to select the structure of each unit to make easy operation and accurate measurement possible.

Figure 4A:
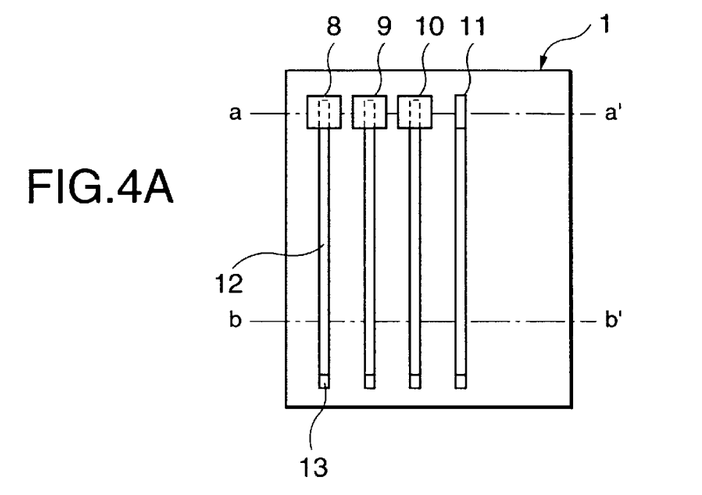
FIG. 4A is a plan view of a sensor element of the urine testing apparatus illustrated in FIG. 2, which is for use in detecting components to be measured.

FIG. 4A shows a plan view of an outlined structure of the principal unit of the sensor element to detect components to be measured in an example of the urine multisensor of the invention. The sensor element 1 (5×6 mm) has the urea detection unit 8 (600×600 $\mu$m), the detection unit of sodium ions 9 (600×600 $\mu$m), and the detection unit of chloride ions 10 (600×600 $\mu$m), a reference electrode 11 (200×600 $\mu$m), a lead unit 12, and a contact electrode 13 (200×200 $\mu$m).

Figure 4B:
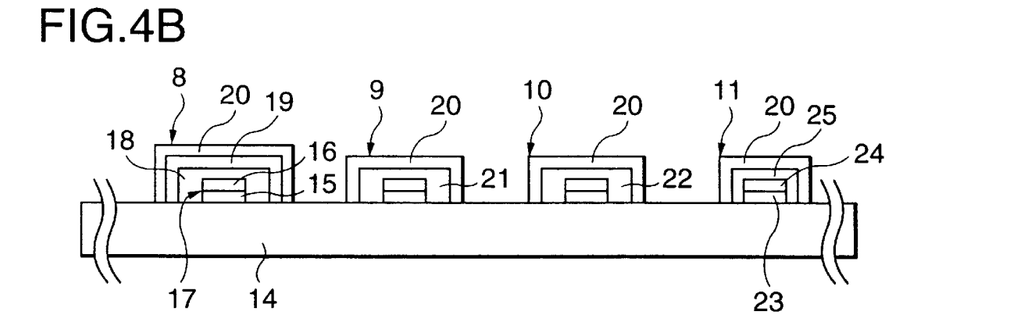
FIG. 4B is an enlarged sectional view taken across a–a' line in FIG. 4A.

FIG. 4B is an enlarged sectional view in a–a' line of the FIG. 4A. As shown in the FIG. 4B, urea detection unit 8 comprises a measurement electrode 17 composed of a titanium layer 15 and a platinum layer 16 that are formed on an insulated base material 14 and a film to detect ammonium ions 18, a film to immobilize urease 19, and a protecting film 20 that are formed on the measurement electrode 17. The insulating base material 14 can be a material selected from a base material having a silicon oxide film formed on a silicon substrate, no-alkali glass, quartz, sapphire. The electrode is made by vacuum evaporation or spattering and the thickness of its film is, for example, 0.02–0.2 $\mu$m in titanium layer and 0.1–0.3 $\mu$m in platinum layer. The material used for the electrode can be gold, iridium, and silver other than platinum. In using silver, it is preferable for use that silver chloride layer is formed on the silver of the measurement electrode unit. For the film 18 to detect ammonium ions, such film is usable as that composed of a substance sensitive to ammonium ions such as nonactin, plasticizer, poly vinylchloride, and for example, that with a thickness of about 1 $\mu$m can be used. The film to immobilize urease 19 formed by adding glutaraldehyde being crosslinking agent to a solution containing urease and bovine serum albumin and its thickness can be, for example, 0.5 $\mu$m for use. The protecting film 20 is put to prevent an effect of a contaminant contained in urine on measurement and can be a fluorine resin, a silicon resin, etc. for use.

The detection unit 9 of sodium ions and the detection unit 10 of chloride ions comprise the measurement electrode 17 made of the titanium layer 15 and the platinum layer 16 that are formed on an insulated base material 14 and a film 21 to detect sodium ions and a film 22 to detect chloride ions made on the measurement electrode 17, and the protecting film 20. On the other hand, the insulating base material, electrode material, the making method of the electrode, and the thickness of electrode film can be the same as urea detection unit 8.

As the film 20 to detect sodium ions, the film composed of, for example, a substance sensitive to sodium ions such as bis(12-crown-4), plasticizer, and poly vinylchloride, can be used and the thickness can be, for example, about 1 $\mu$m. As the film 21 to detect chloride ions, the film composed of, for example, a substance sensitive to chloride ions such as tetraacetylammonium salt, plasticizer, and poly vinylchloride, can be used and the thickness can be, for example, about 1 $\mu$m. As the protecting film 20, the same structure as the urea detecting unit can be used.

The reference electrode 11 can be made by forming a silver layer 23 on the insulated base material 14 and then, processing the surface of the silver layer to make a silver chloride layer 24. Improvement of contactivity can be achieved by layering of titanium and platinum as undercoats of the silver layer 23. These films are formed by the vacuum evaporation and the spattering and the thickness of the silver layer can be, for example, 0.1–1.0 $\mu$m. The layer of silver chloride can be made by treating with an aqueous solution of iron chloride (III) or chromium chloride (III) or by electrolysis in an aqueous solution of a chloride compound. It is preferable to increase in the stability of the reference electrode that the film 25 of electrolytic gel containing potassium chloride and the protecting film 20 are further formed on the layer of silver chloride. As a forming material of the film 25 of electrolytic gel, polyvinyl alcohol can be used. For the protecting film 20, the same structure as the urea detecting unit can be used.

Figure 4C:
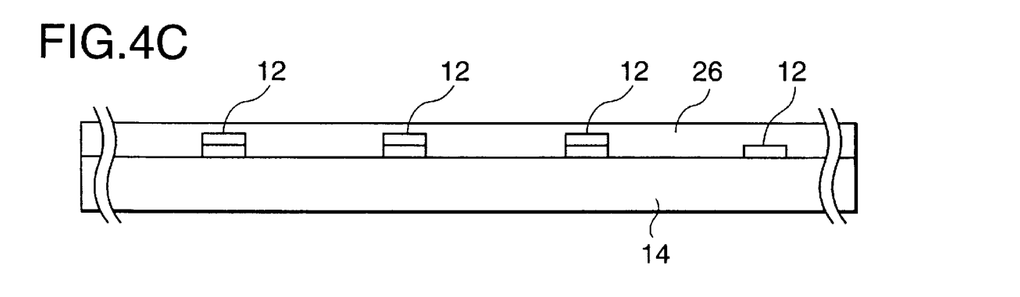
FIG. 4C is an enlarged sectional view taken across b–b' line in FIG. 4A.

FIG. 4C is the enlarged sectional view in the b–b' of FIG. 4A and shows the structure in which the lead unit 12 is formed on the insulated base material 14 that is covered by a polyimide insulating film.

The following is the operation of the urine multisensor with aforementioned structure. First in the urine detection unit 5, urea molecule contained in a urine sample solution is converted to ammonium ions and carbon dioxide gas by the action of urease. These ammonium ions reacts to a substance sensitive to ammonium ions to change a surface electric potential on the measurement electrode. The voltage change is detected as a change in contrast to the reference electrode through the voltage detecting circuit 2. The voltage change is outputted to signal processing unit as a signal to convert to urea concentration.

In the detection unit 6 of sodium ions, sodium ions contained in the urine sample solution bind to a substance sensitive to sodium ions to change a surface electric potential on the measurement electrode. The voltage change is detected as a change in contrast to the reference electrode through the voltage detecting circuit 2. The voltage change is outputted to signal processing unit 3 as a signal to convert to the concentration of sodium ions. Also in the detection unit of chloride ions 7, on the basis of binding to a substance sensitive to chloride ions, a change of the surface electric potential on the measurement electrode is detected and the voltage change is converted to the concentration of chloride ions.

The signal processing unit 3 comprises a CPU (central processing unit), a ROM (read only memory), a RAM (random access memory), an A/D converter (analog/digital converting device), converts a signal from voltage detecting circuit to a digital signal using the A/D converter to work CPU for converting the signal to urea concentration, the concentration of sodium ions, and the concentration of chloride ions according to a program stored in the ROM, and finally stores in RAM. Next, the CPU processes the stored data of these concentrations to determine the urine specific gravity according to a program based on any one of the formulae (2), (3), and (4) and stored in ROM. Display unit 4 for concentration of components to be measured comprises LCD (display made of liquid crystals) and display controlling unit to display any desired item among the urine specific gravity, the urea concentration, the concentration of sodium ions, and the concentration of chloride ion that are known in the signal processing unit. Other than the urine specific gravity, for example, the concentration of sodium ions and the concentration of chloride ion can be optionally displayed as a matter of convenience.

Figure 5A:
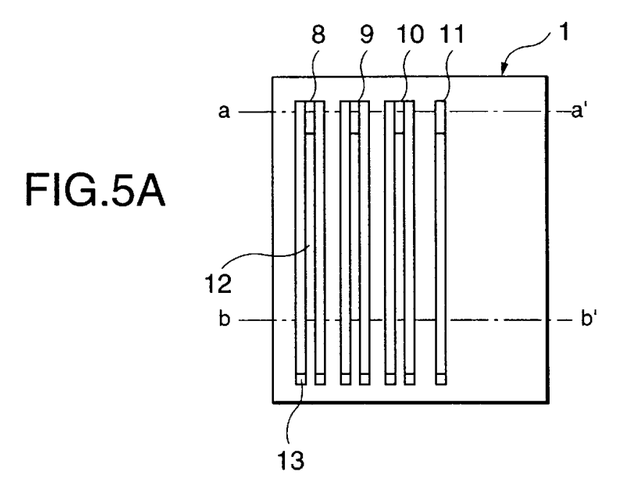
FIG. 5A is a plan view of the sensor element of the urine testing apparatus illustrated in FIG. 2, in which the device has been fitted with a measurement electrode made from an ion-seneitive field-effect transistor (ISFET)
Figure 5B:
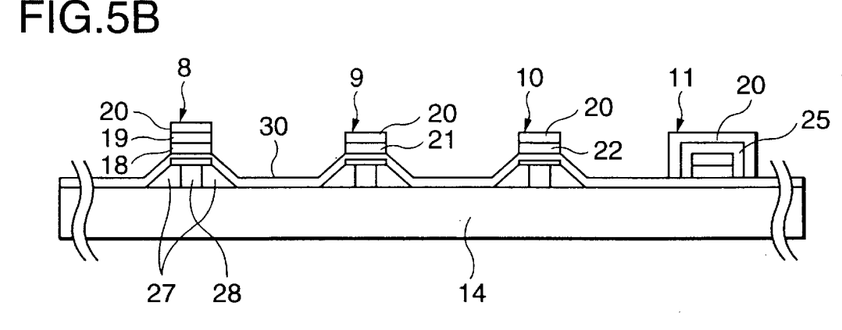
FIG. 5B is an enlarged sectional view taken across a–a' line in FIG. 5A.

FIG. 5A is a plan view of an ion-sensitive field-effect transistor (ISFET) used as the measurement electrode of the sensor 1, of the urine multisensor of the invention, to detect components to be measured. The size of the sensor element 1 is 5×6 mm and has a structure composed of the urea detection unit 8 (200×600 $\mu$m),the detection unit of sodium ions 9 (200×600 $\mu$m), and the detection unit of chloride ions 10 (200×600 $\mu$m), a reference electrode 11 (200×600 $\mu$m), a lead unit 12, and a contact electrode 13 (200×200 $\mu$m). FIG. 5B is an enlarged sectional view in a–a' line of the FIG. 5A. On the insulating base material 14, ISFET is formed with the composition of an n-type silicon region 27, a p-type silicon region 28, a silicon oxide film 29, and a silicon nitride film 30. The transistor can be prepared by, for example, the method to form using an island-like silicon layer put on the sapphire base material described in the publication of (unexamined) patent applications 1992-26054 and also by using such silicon base material as "silicon on insulator" (SOI) base material. Further, The same preparation becomes possible by using amorphous silicon or polysilicon as an insulated base material mounted on glass or quartz. Other than silicon nitride film herewith shown as an ion sensitive film, tantalum oxide film and aluminium oxide film are also used.

The urea detection unit 8 has a structure comprising detecting film 18 for ammonium ions, a film 19 to immobilize urease, and the protecting film 20 on the ISFET. For the detecting film 18 for ammonium ions, a poly vinylchloride film containing such substance sensitive to ammonium ions as nonactin can be used; the thickness of the film can be 1 $\mu$m. The film 19 to immobilize urease can be formed by adding glutaraldehyde as a crosslinking agent to a solution containing urease and bovine serum albumin for use; the thickness of the film can be 0.5 $\mu$m. The protecting film 20 is formed to prevent an effect of contaminants contained in urine on measurement and can be formed from a fluorine resin and a silicon resin.

Figure 5C:
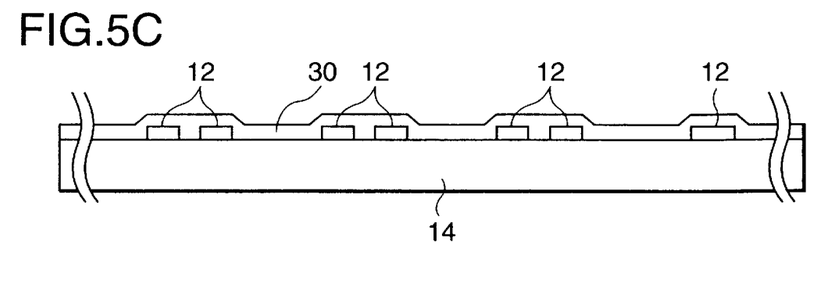
FIG. 5C is an enlarged sectional view taken across b–b' line in FIG. 5A.

The detection unit 9 of sodium ions and the detection unit 10 of chloride ions have structures comprising a film 21 to detect sodium ions, a film 22 to detect chloride ions, and the protecting film 20 on ISFET. For the film 21 to detect sodium ions, a poly vinylchloride film containing a substance sensitive to sodium ions such as bis(12-crown-4) can be used; the thickness of the film can be 1 $\mu$m. For the film 22 to detect chloride ions, a poly vinylchloride film containing a substance sensitive to chloride ions such as tetraacetylammonium salt can be used; the thickness can be about 1 $\mu$m. For the reference electrode 11, the same description as that of the FIG. 4 is applied. FIG. 5C is the enlarged sectional view in the b–b' of FIG. 5A and shows the structure in which the lead unit 12 composed of the region of electroconductive silicon is formed on the insulated base material 14, of which whole unit is covered by a silicon nitride film 30.

Aforementioned urine multisensor has a structure preferable to know the urine specific gravity and fitted with both the detection unit of sodium ions and the detection unit of chloride ions; a structure having one of them can be used.

Next, referring to FIGS. 6 through 8C, description will proceed to a urine multisensor preferable to measure the urinary glucose value corrected with the urine specific gravity as a urine testing apparatus according to a second embodiment of the present invention.

Figure 6:
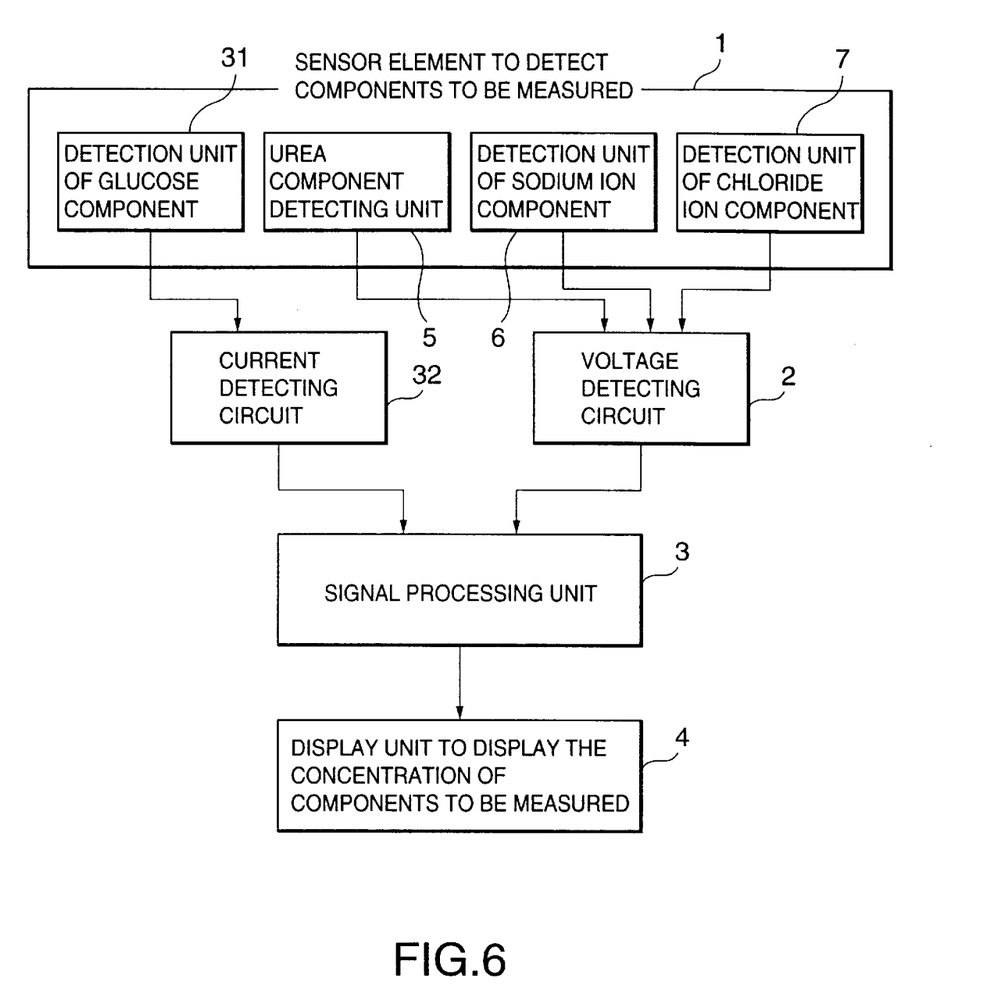
FIG. 6 is a block diagram for showing a structure of a urine testing apparatus for measurement of a urinary glucose value according to a second embodiment of the present invention.

FIG. 6 is a block diagram to show a structure of the urine multisensor for measurement of the urinary glucose value. As illustrated in FIG. 6, the urine multisensor comprises the sensor element 1 to detect components to be measured, a current detecting circuit 32, a voltage detecting circuit 2, signal processing unit 3, and a display unit 4 to display the concentration of components to be measured. The sensor element 1 to detect components to be measured comprises the glucose detecting unit 31, the urea detection unit 5, the detection unit of sodium ions 6, and the detection unit of chloride ions 7.

Figure 7:
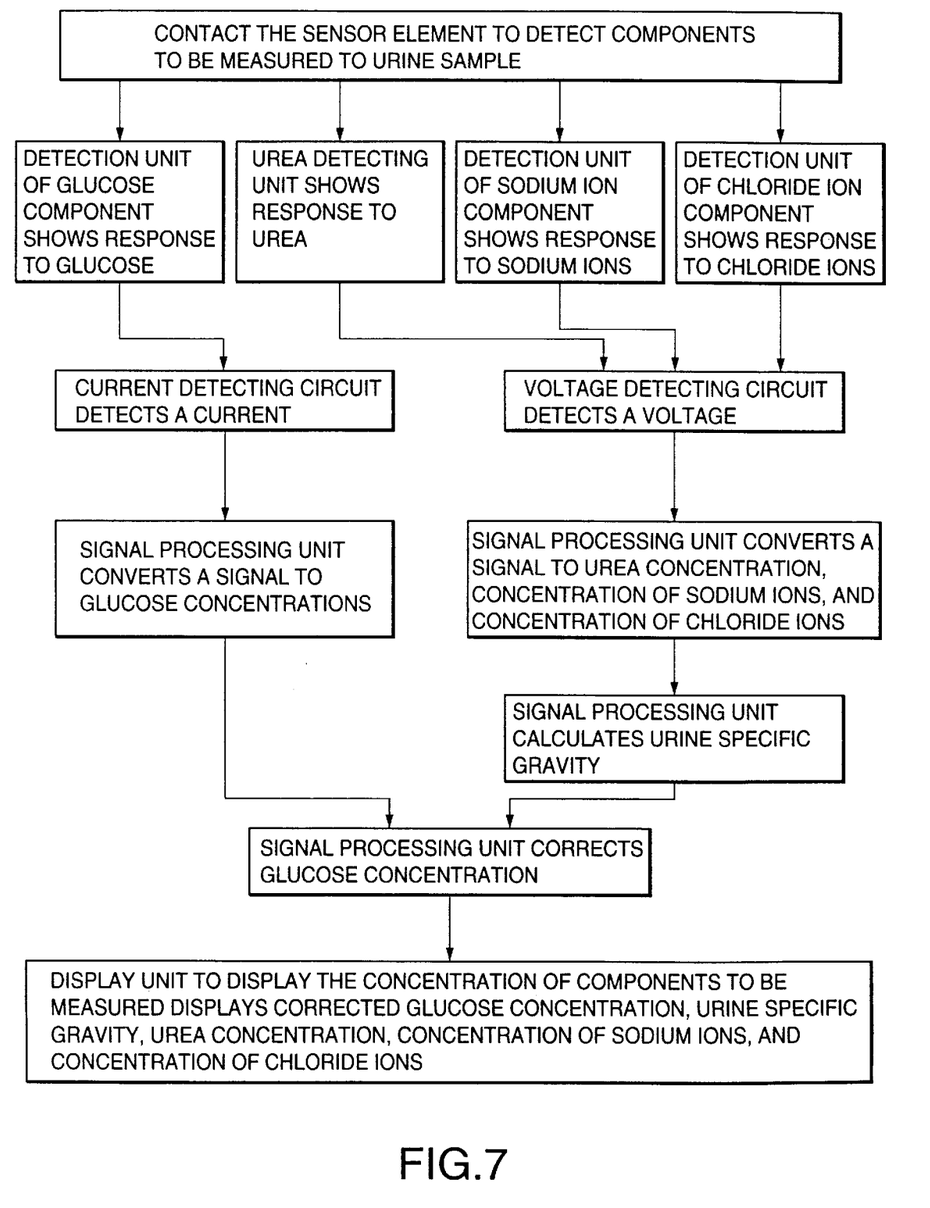
FIG. 7 is a flow chart for showing an operation of the urine testing apparatus illustrated in FIG. 6.

FIG. 7 is a flow chart for showing an operation of the urine multisensor for measurement of the urinary glucose value. The measurement of the urinary glucose value with the urine multisensor for the measurement of the urinary glucose value is described herewith using the figure. By contacting the sensor element of the urine multisensor to detect components to be measured to the sample of urine, the glucose detection unit, the urea detection unit, the detection unit of sodium ions, and the detection unit of chloride ions show response to glucose, urea, sodium ions, and chloride ions contained in urine, respectively. As a result of the reaction, a current generated in the glucose detection unit is detected through the current detecting circuit and a voltage occurred each in the urea detection unit, the detection unit of sodium ions, and the detection unit of chloride ions are detected through the voltage detecting circuit. In the signal processing unit, a signal outputted from the current detecting circuit is converted to the concentration of glucose and a signal outputted from the voltage detecting circuit is converted to each of the concentration of urea, the concentration of sodium ions, and the concentration of the chloride ions. Next, as same as the case described in the FIGS. 1–4, the urine specific gravity is calculated from the concentration of urea and at least one of the concentration of sodium ions and the concentration of the chloride ions. Finally, the concentration of glucose is corrected with the urine specific gravity according to the following formula (5).

$$\text{Urinary glucose value (specific gravity corrected)} = \text{urinary glucose value} \times (1.015 - 1.000)/(\text{urine specific gravity} - 1.000) \quad (5)$$

The display unit 4 to display the concentration of components to be measured displays a desired item among the concentration of glucose, the concentration of urea, the urine specific gravity, the concentration of sodium ions, and the concentration of the chloride ions that have been corrected. Other than the corrected concentration of glucose, the urine specific gravity, and at least one of the concentration of sodium ions and the concentration of chloride ions can be optionally displayed as a matter of convenience.

Figure 8A:
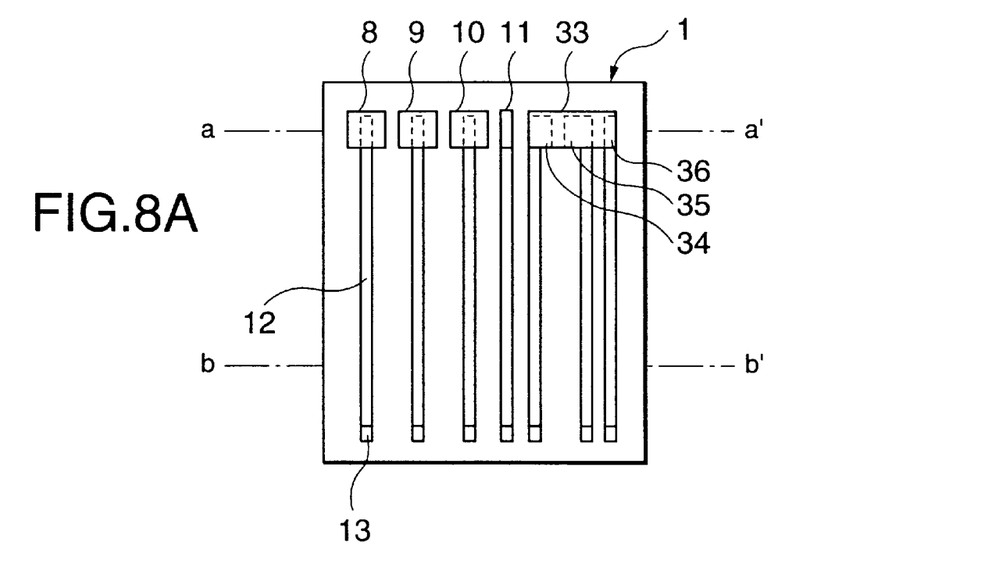
FIG. 8A is a plan view of a sensor element of the urine testing apparatus illustrated in FIG. 6, which is for use in detecting components to be measured.
Figure 8B:
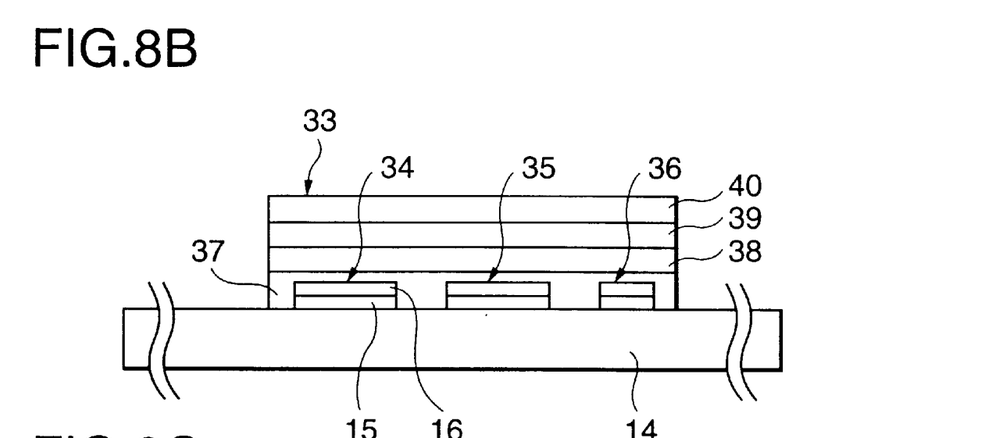
FIG. 8B is an enlarged sectional view taken across a–a' line in FIG. 8A.

FIG. 8A is a plan view of the sensor element 1 of the urine multisensor, of the invention, to detect components to be measured. The size of the sensor element 1 is 5×6 mm and has a structure comprising the glucose detection unit 33 (1400×600 $\mu$m), the urea detection unit 8 (600×600 $\mu$m), the detection unit of sodium ions 9 (600×600 $\mu$m), and the detection unit of chloride ions 10 (600×600 $\mu$m), a reference electrode 11 (200×600 $\mu$m), a lead unit 12, and a contact electrode 13 (200×200 $\mu$m). FIG. 8B is an enlarged sectional view of the glucose detection unit 33 in a–a' line of the FIG. 8A. The glucose detection unit 33 has a structure comprising a working electrode 34 and a counter electrode 35 formed on the insulated base material 14, a reference electrode 36, a film 37 formed on these electrodes to remove a disturbing substance, a film 38 to immobilize glucose oxidase, a film 39 restrict the permeation of glucose. The insulated base material 14 can be composed of a material selected from a base material formed by covering silicon with silicon oxide film, no-alkali glass, quartz, and sapphire. The working electrode 34 and the counter electrode 35 are titanium layer 15 and platinum layer 16 formed by vacuum evaporation or spattering; the thickness of these films is 0.02–0.2 $\mu$m in titanium layer and 0.1–0.3 $\mu$m in platinum layer. The material used for the electrode can be gold, palladium, or iridium other than platinum. The reference electrode can be made by forming a silver layer on the insulated base material followed by that silver chloride layer is formed by surface treatment of the silver layer. Improvement of contactivity can be achieved by layering of titanium and platinum as undercoats of the silver layer 23. These films can be formed by the vacuum evaporation and the spattering; the thickness of the silver layer can be 0.1–0.3 $\mu$m. The layer of silver chloride can be made by treating with an aqueous solution of iron chloride (III) or chromium chloride (III) or by electrolysis in an aqueous solution of a chloride compound.

The film 37 formed to remove a disturbing substance can be formed by using at least one material selected from silane coupling agent, Nafion, and acetyl cellulose. The film 38 to immobilize glucose oxidase can be made by dropping an aqueous solution containing glucose oxidase, albumin, and glutaraldehyde. The film 39 to restrict the permeation of glucose can be formed a material selected from silicon, carboxymethyl cellulose, polyurethane, fluorine resin. The protecting film 40 can be formed by using fluorine resins and silicon resins; the thickness of the film can be 1 $\mu$m.

In aforementioned examples, the three-electrode structure composed of the working electrode made on the insulated base material, the counter electrode, and the reference electrode has been described for the glucose detection unit 33. However, a two-electrode structure composed of only the working electrode and the counter electrode can detect glucose. A structure composed of the urea detection unit 8, the detection unit 9 of sodium ions, the detection unit 10 of chloride ions, the reference electrode 11 can be, for example, the structure described for the FIG. 4.

Figure 8C:
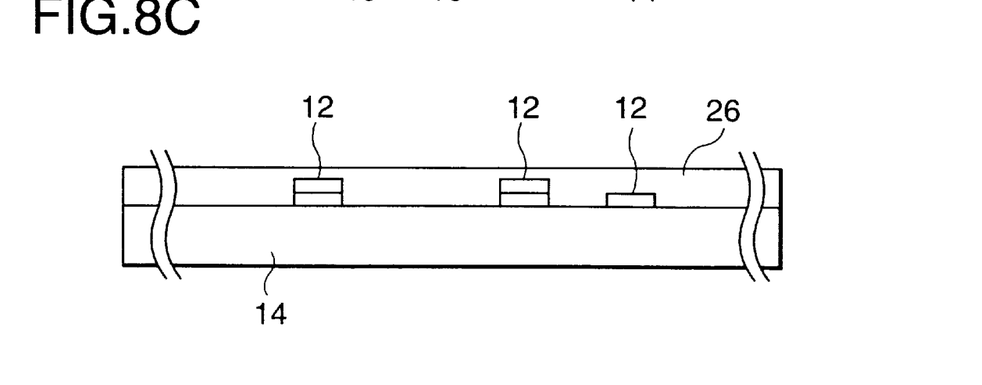
FIG. 8C is an enlarged sectional view taken across b–b' line in FIG. 8A.

FIG. 8C is the enlarged sectional view in the b–b' of FIG. 8A, of which structure has the lead unit 12 formed on the insulated base material 14 that is covered by a polyimide insulating film 26.

The operation of the urine multisensor of the second embodiment is described in further detail with reference to FIGS. 7 and 8. In the glucose detecting unit 31, the glucose molecules of a urine sample are converted to D-glucono-δ-lactone and hydrogen peroxide by the action of glucose oxidase in the film for immobilizing glucose oxidase. The hydrogen oxide is oxidized on the surface of the working electrode to generate a current from the working electrode to the counter electrode. The current detecting circuit 3 named potentiostat applies a voltage of 0.7 V to the working electrode against the reference electrode in order to oxidize hydrogen peroxide, changes the electric potential of the counter electrode to keep the voltage, and then measures the oxidation current of hydrogen peroxide running from the working electrode to the counter electrode. The current is outputted to the signal processing unit 3. Processing for the urea detection unit 5, the detection unit of sodium ions 6, and the detection unit of chloride ions 7 is quite same as that of the case of the FIG. 3. The voltage change corresponding to each component is detected by the voltage detecting circuit 2 and outputted to the signal processing unit 3. The signal processing unit 3 comprises a CPU (central processing unit), a ROM (read only memory), a RAM (random access memory), and A/D converter (analog/digital converting device), converts a signal from the current detecting circuit 32 and the voltage detecting circuit 2 to a digital signal using the A/D converter to work CPU for converting the signal to each glucose concentration, urea concentration, the concentration of sodium ions, and the concentration of chloride ions according to a program stored in the ROM, and finally stores in RAM. Next, the CPU processes the stored data of the urea concentration, the concentration of sodium ions, and the concentration of chloride ions to determine the urine specific gravity according to a program based on any one of aforementioned formulae (2)–(4) and stored in ROM and then, stores the result in the RAM. Following these steps, the CPU executes the process of calculation of corrected glucose concentration using the glucose concentration and the urine specific gravity that have been stored in RAM, on the basis of the formula (5) stored in ROM and finally saves in the RAM. Display unit 4 for concentration of components to be measured comprises LCD (display made of liquid crystals) and display controlling unit to read the glucose concentration, the urine specific gravity, the urea concentration, the concentration of sodium ions, and the concentration of chloride ion of which all are corrected and stored in RAM by a command of the CPU and to display them on an LCD.

In the aforementioned examples, a signal from the sensor element to detect components to be measured is detected by the current detecting circuit or the voltage detecting circuit to output to the signal processing unit for calculation of the concentration of each component to be measured. However, the structure of the sensor element to detect components to be measured, detecting circuit, and the signal processing unit is not restricted to this one and can be the structure capable of measuring the urine specific gravity and calculating the urinary glucose value corrected with the urine specific gravity that are the purpose of the invention. The structure illustrated herewith is a preferable one for productivity, handling, etc.

EXAMPLES

Example 1

The following result was yielded by the measurement of a urine sample by using the urine multisensor illustrated in the FIG. 1 and having the structure that has the sensor element, illustrated in the FIG. 3 or the FIG. 4, to detect components to be measured of the structure.

TABLE 1

| | |
|---|---|
| urea concentration | 1075 mg/dl |
| concentration of sodium ions | 373 mg/dl |
| concentration of chloride ion | 671 mg/dl |
| urine specific gravity (calculated) | 1.024 |
| urine specific gravity (measured) | 1.025 |

From the result of the Table 1, the urine specific gravity known from the urine multisensor of the invention well corresponds to the measured value.

Example 2

The urine specific gravity and the urinary glucose value of the partial urine were measured 9 times a day by using the urine multisensor, illustrated in the FIG. 5, having the structure that has the sensor element, illustrated in the FIG. 7, to detect components to be measured of the structure. The urinary glucose value of total urine excreted for 24 hours was 8.6 mg/dl.

TABLE 2

| Sample number | Urine specific gravity | Urine glucose value (mg/dl) | Corrected urinary glucose value (mg/dl) |
|---|---|---|---|
| 1 | 1.017 | 9.3 | 8.4 |
| 2 | 1.010 | 4.5 | 7.0 |
| 3 | 1.011 | 4.3 | 6.1 |
| 4 | 1.018 | 10.5 | 8.7 |
| 5 | 1.020 | 11.8 | 9.0 |
| 6 | 1.027 | 21.3 | 11.8 |
| 7 | 1.026 | 20.0 | 11.8 |
| 8 | 1.008 | 4.3 | 8.5 |
| 9 | 1.017 | 7.5 | 6.8 |

From the result of the Table 2, the corresponding ratio to the urinary glucose value of the total excreted urine was 175% in the measured urinary glucose value in contrast to 8% in the corrected urinary glucose value; the corrected urinary glucose value well reflects the urinary glucose value of the total excreted urine.

As described above, the primary effect of the invention is to realize the easy and accurate measurement of the urine specific gravity by using a small urine test apparatus. The effect is based on the measurement of urea concentration and at least one of the concentration of sodium ions and the concentration of chloride ions that are contained in urine and calculate the urine specific gravity from the urea concentration and at least one of the concentration of sodium ions and the concentration of chloride ions.

Further, the secondary effect of the invention is to make possible to know the urinary glucose value of total urine excreted for 24 hours simply by measuring the urinary glucose value of the partial urine. Thus, a small urine test apparatus easily and reliably make to measure the urinary glucose value possible. The effect is based on the measurement of the urinary glucose value and the urine specific gravity of the partial urine to correct the urinary glucose value with the urine specific gravity for knowing the urinary glucose value of total urine excreted for 24 hours.

As mentioned above, according to the present invention, the urine specific gravity is easily and accurately known from the urea concentration, the concentration of sodium ions, or the concentration of the chloride ions contained in urine, or both these concentrations. By correcting the urinary glucose value with urine specific gravity yielded, the urinary glucose value corresponding to the total urine excreted for 24 hours can be easily and accurately measured even in the case of the sample of the partial urine.

While the present invention has thus far been described in conjunction with a preferred embodiment thereof, it will be readily possible for those skilled in the art to put the present invention into various other manners.

What is claimed is:

1. A urine testing apparatus comprising:
   a sensor element, to detect components to be measured, having a urea detecting unit and at least one of a detection unit of sodium ions and a detection unit of chloride ions to detect urea and at least one of sodium ions and chloride ions that are components to be measured contained in urine;

a signal processing unit for converting a signal generated by detecting each component to be measured in said sensor element to detect components to be measured to a concentration of each component to be measured and for calculating a specific gravity of the urine on the basis of these concentrations; and a display unit for displaying the urine specific gravity calculated in said signal processing unit and the concentration of at least one of the components to be measured.

2. A urine testing apparatus as claimed in claim 1, wherein a voltage detecting circuit detects a voltage signal generated by detecting the components to be measured using said sensor element to detect components to be measured and said signal processing unit converts a detection signal of each component to be measured outputted from said voltage detecting circuit to the concentration of each component to be measured and calculates the urine specific gravity from the concentrations.

3. A urine testing apparatus as claimed in claim 1, wherein said urine testing apparatus calculates the urine specific gravity on the basis of any one of a concentration of sodium ions or a concentration of chloride ions and a concentration of urea.

4. A urine testing apparatus as claimed in claim 1, wherein said urine detecting unit comprises a measurement electrode and a reference electrode, that are formed on an insulated base material, and a urea detecting film formed on said measurement electrode and containing urease.

5. A urine testing apparatus as claimed in claim 4, wherein said measurement electrode is an ion-sensitive field-effect transistor.

6. A urine testing apparatus as claimed in claim 1, wherein said sensor element, to detect components to be measured, has both said detection unit of sodium ions and said detection unit of chloride ions in addition to said urea detecting unit, said detection unit of sodium ions, said detection unit of chloride ions and said urea detecting unit having a measurement electrode and a reference electrode formed on an insulated base material and a film for detecting components to be measured, that contains a substance sensitive to sodium ions and a substance sensitive to chloride ions formed on the measurement electrode.

7. A urine testing apparatus as claimed in claim 6, wherein said measurement electrode is an ion-sensitive field-effect transistor.

8. A urine testing apparatus comprising:

a sensor element, to detect components to be measured, having a glucose detecting unit, a urea detecting unit, and at least one of a detection unit of sodium ions and a detection unit of chloride ions to detect glucose, urea and at least one of sodium ions and chloride ions that are components to be measured contained in urine;

a signal processing unit for converting a signal generated by detecting each component to be measured in said sensor element to detect components to be measured to a concentration of each component to be measured and for calculating a specific gravity of the urine on the basis of a concentration of urea and at least one of a concentration of sodium ions and a concentration of chloride ions to correct the concentration of glucose with the urine specific gravity obtained; and a display unit for displaying the glucose concentration corrected in said signal processing unit, and at least one of the urine specific gravity, the urea concentration, a concentration of sodium ions and a concentration of chloride ions.

9. A urine testing apparatus as claimed in claim 8, wherein a current detecting circuit detects a current signal generated by detecting glucose with said sensor element to detect components to be measured, a voltage detecting circuit detects a voltage signal generated by detecting urea and at least one of sodium ions and chloride ions, and said signal processing unit converts the current and the voltage signals outputted from said current detecting circuit and said voltage detecting circuit into the concentration of each component to be measured, respectively, and calculates the urine specific gravity and a glucose concentration corrected by the urine specific gravity on the basis of the concentrations.

10. A urine testing apparatus as claimed in claim 8, wherein said sensor element to detect components to be measured has a glucose detecting unit, a urine detecting unit, and any one of a detection unit of sodium ions and a detection unit of chloride ions to calculate the urine specific gravity on the basis of any one of a concentration of sodium ions and a concentration of chloride ions, and the urea concentration.

11. A urine testing apparatus as claimed in claim 8, wherein said glucose detecting unit has a structure comprising a measurement electrode and a reference electrode, that are formed on an insulated base material, and a detecting film, that is formed on the electrode, for components to be measured including glucose oxidase and said measurement electrode is a working electrode or a working electrode and a counter electrode.

12. A urine testing apparatus as claimed in claim 8, wherein said urine detecting unit comprises a measurement electrode and a reference electrodes that are formed on an insulated base material, and a urea detecting film formed on said measurement electrode and containing urease.

13. A urine testing apparatus as claimed in claim 11, wherein said measurement electrode is an ion-sensitive field-effect transistor.

14. A urine testing apparatus as claimed in claim 8, wherein said sensor element, to detect components to be measured, has both said detection unit of sodium ions and said detection unit of chloride ions in addition to said urea detecting unit, said detection unit of sodium ions, said detection unit of chloride ions and said urea detecting unit having a measurement electrode and a reference electrode formed on an insulated base material and a film for detecting components to be measured, that contains a substance sensitive to sodium ions and a substance sensitive to chloride ions formed on the measurement electrode.

15. A urine testing apparatus as claimed in claim 14, wherein asid measurement electrode is an ion-sensitive field-effect transistor.

* * * * *